United States Patent
Erdman et al.

(10) Patent No.: US 7,963,953 B2
(45) Date of Patent: Jun. 21, 2011

(54) ARTICLE WITH ADJUSTABLE ELASTOMERIC WAIST BELT

(75) Inventors: Edward P. Erdman, West Chester, PA (US); Michael J. Naughton, Attleboro, MA (US); Stacy J. Driskell, Royersford, PA (US)

(73) Assignee: First Quality Retail Services, LLC, Great Neck, NY (US)

( * ) Notice: Subject to any disclaimer, the term of this patent is extended or adjusted under 35 U.S.C. 154(b) by 711 days.

(21) Appl. No.: 11/904,407

(22) Filed: Sep. 27, 2007

(65) Prior Publication Data

US 2008/0071240 A1 Mar. 20, 2008

Related U.S. Application Data

(63) Continuation-in-part of application No. 11/241,777, filed on Sep. 30, 2005, now abandoned.

(51) Int. Cl.
*A61F 13/15* (2006.01)
(52) U.S. Cl. ...... 604/385.3; 604/385.03; 604/385.24; 604/385.26; 604/385.28; 604/385.29
(58) Field of Classification Search .......... 604/385.03, 604/385.24, 385.26, 385.28, 385.29, 385.3
See application file for complete search history.

(56) References Cited

U.S. PATENT DOCUMENTS

| | | | |
|---|---|---|---|
| 5,439,458 A | 8/1995 | Noel | |
| 2002/0147438 A1* | 10/2002 | Tanaka et al. | 604/392 |
| 2002/0156449 A1 | 10/2002 | Kling | |
| 2005/0267431 A1 | 12/2005 | Sasaki | |

OTHER PUBLICATIONS

International Search Report, dated Nov. 24, 2008, for PCT/US08/78132.
Written Opinion of the International Searching Authority, dated Nov. 24, 2008, for PCT/US08/78132.

* cited by examiner

*Primary Examiner* — Jacqueline F Stephens
(74) *Attorney, Agent, or Firm* — Amster, Rothstein & Ebenstein LLP

(57) ABSTRACT

A disposable absorbent article includes a main body, a sleeve-like member extending adjacent the waist edge of the front or rear portions, and an adjustable elastomeric waist belt having a central portion and a pair of opposite free ends each defining ear-like projections. The central portion of the elastomeric member can be disposed in a sleeve-like member with each ear-like projection extending out from opposite sides. The central portion can be attached to the sleeve-like member and/or the main body near a longitudinal axis of the main body or adjacent the waist edge of the main body. The ear-like projections can be attachable to each other or the main body to form the desired waist size of the wearer of the absorbent article.

26 Claims, 7 Drawing Sheets

ARTICLE WITH ADJUSTABLE ELASTOMERIC WAIST BELT

CROSS REFERENCE TO RELATED APPLICATION

The present application is a continuation-in-part of U.S. patent application Ser. No. 11/241,777, filed Sep. 30, 2005, and entitled "Elastomeric Ear Construction For Disposable Absorbent Article."

BACKGROUND

The present invention relates to the field of absorbent articles used for the containment of body fluids. More particularly the invention relates to the use of elastomeric ears for fitting these articles on the body of the wearer.

Disposable absorbent articles have long been used for the absorption of various kinds of bodily fluids. They have been used in various forms ranging from diapers for babies, to adult incontinence articles, to feminine health care products. Today, most of these articles employ the use of an absorbent pad sandwiched between a liquid permeable sheet and a liquid impermeable sheet. These articles may take various shapes and sizes depending upon their need and applicability. For example, a pad type structure may be used for feminine health care products. The article may be hourglass-shaped for use as a baby diaper, or it may take the shape of pants when it is used for toilet training for young children, or as a convenience device for adults having difficulty controlling their bladder.

Considerable effort has been expended by engineers to increase the use of the absorbent articles. This effort has been directed towards increasing functionality of the article, for example, by improving absorption, retention of multiple voids, less leakage, and enhancing ease of use and wearer comfort, such as improving fit and minimizing skin irritation. Further efforts include designing a better-looking product, by using printed backsheets and reducing the product's bulkiness. Other innovations include features such as visual indicators of "time to change" the article, "glow in the dark" articles, and articles with skin conditioners, etc.

Since such an article is usually worn throughout the day, it is very important to not only minimize skin irritation that may be caused by the article, but also to maximize the fit of the article on the body so as to increase the comfort of the wearer. Ease in wearing, cozy fitness for long periods of time, and freedom in body movement are just some of the desired features from such a product.

Diapers are one kind of absorbent article that have evolved over time from bulky, uncomfortable, leak prone, rectangular articles, to lightweight, long lasting, appealing looking products. Owing to the research and development in the field, the acceptability of diapers has increased to such an extent that they enjoy a 95% penetration in the US market.

One important area where significant development has occurred is in the way the diaper is fitted to the body. The hourglass-shaped design is one such innovation that was adopted by the industry in the 1980s. In the hourglass-shaped configuration, the diaper has a near rectangular crotch region. Above and below this region (i.e., at the shorter side of the rectangle) are relatively broad front and rear portions of the diaper. These sections together cover the front (i.e., the area above the crotch and below the stomach) and back portion (i.e., the bottom) of the wearer. The top edge of these sections (i.e., the front and rear) together form the waist portion of the diaper.

In order to have better coverage of the side portion of the body when a diaper is worn, these sections are progressively being redesigned with flaps projecting outwardly from both sides of the diaper. These flaps or "ears" not only give a fuller coverage to the body (and hence provides a better fit), but also provide a well-defined leg section.

The hourglass-shaped configuration as is commonly used today has relatively broad front and rear portions (with wing like protrusions) connected by a crotch section having an absorbent member. When a diaper is worn, it is positioned in such a way that the absorbent section covers the crotch of the wearer and the front section is folded over so as to cover the front portion of the wearer. The rear portion covers the bottom of the wearer. The outward projecting ears of the front portion (from the navel to the side of the body) are overlapped by the outwardly projecting ears from the rear portion (coming from the back of the body to the front). In this way, a full waist circle is formed. As mentioned earlier, the ears can be shaped in such a way so as to have well-defined leg openings.

In order for the diaper to stay in place there should be some way for the rear ears to be fixed to the front portion of the diaper. The industry has adopted various means for achieving this result, such as through the use of tapes and/or mechanical fasteners. Since fasteners such as tapes and other fasteners have a tendency to gradually loosen their grip during prolonged periods of wearing the diaper, it is desirable to have a configuration of ears and fasteners such that the diaper can be pulled and tightly fitted on the wearer. This would ensure a prolonged period of comfortable wearing.

U.S. Pat. No. 5,496,298 to Kuepper et al. discloses the construction of such ears. The ears disclosed in the reference are attached to the front and rear portions of the main body of the diaper. The ears are made of elastomeric material (for better body hugging fit), and are shaped to cover the side of the body (increasing leak protection). The ears are disclosed as being affixed to the body of the diaper along proximal edges at the outer periphery of the diaper. This type of attachment provides only limited room for expansion around the body of the wearer. Accordingly, the area available for increasing the waist fit in this configuration is only the ear portion. Therefore, increasing the stress on these ears can put a strain on the side of the body. Furthermore, since a small portion of material is available for providing a proper fit, the material is required to be of high quality. High quality elastomers add to the cost of the article.

U.S. Pat. No. 6,648,868 to Sayama et al. discloses the use of two bands of elastic members at the top and bottom edge of the front as well as the rear portion of the diaper. Although this configuration may have better performance in terms of leak protection, the use of elastic at the edges would strain the edges and consequently cut into the skin, making it difficult to wear the article for prolonged periods of time.

U.S. Patent Publication No. 2002151863 A1 to Toyoshima discloses the use of two elastic members at either side of the absorbent core. In such a configuration, the use of an elastic may irritate the skin. Furthermore, since the elastic is only provided along the sides of the article, the grip at the back of the body is not provided for.

Accordingly, it would be desirable to provide an absorbent article that not only has a better grip around the waist of the wearer, but is also minimally irritable to the skin. This would increase the prolonged continuous wearing of the article. It is also desirable to achieve such an article with minimal cost. The present invention has an objective to overcome the aforementioned drawbacks, and provide a better absorbent article.

Additional objectives of the present invention include providing a better fitting absorbent article, providing an absorbent article that is comfortable to wear for long periods of time, and providing a better fitting and comfortable absorbent article by using cost-effective material.

SUMMARY

The disposable absorbent article with an adjustable elastomeric waist belt can generally comprise a main body having a front portion, a rear portion, a crotch portion extending therebetween, a sleeve-like member extending adjacent the waist edge of the front or rear portions, and an elastomeric member having a central portion and a pair of opposite free ends each defining ear-like projections. The central portion of the elastomeric member can be disposed in the sleeve-like member with each ear-like projection extending out from opposite sides of the sleeve-like member. The central portion can be attached to the sleeve-like member or the main body near a longitudinal axis of the main body and/or adjacent the waist edge of the main body. The ear-like projections can be attachable to each other or the main body to form the desired waist size of the wearer of the absorbent article. In another embodiment of the article, the elastomeric member can have a pair of elastomeric members each having one end retained within the sleeve-like member and an opposite free end extending from the sleeve-like member and defining an ear-like projection.

Other advantages and features of the absorbent article may become apparent from the following detailed description, when considered in conjunction with the appended drawing figures.

DETAILED DESCRIPTION

Figure 1:
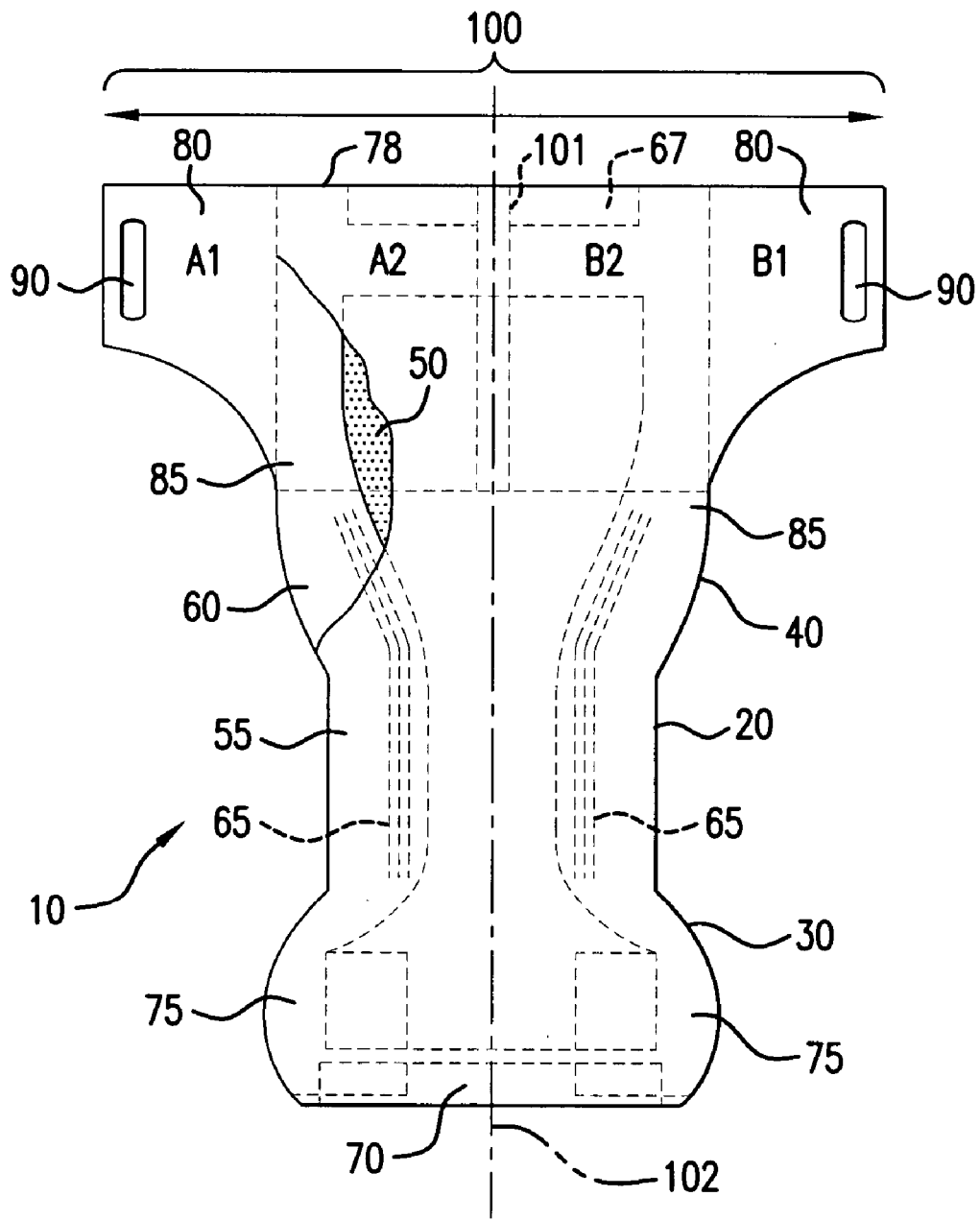
FIG. 1 is the top view of the absorbent article of one embodiment of the invention.

The present invention relates to absorbent articles that are disposable in nature. The term "disposable absorbent article" as mentioned herein refers to articles that absorb and contain body discharges. The articles are discarded after a first use and are not intended to be used more than once. The invention is more particularly described below with reference to hourglass-shaped absorbent articles that are placed close to the body and wrapped over so as to form an underwear-like structure. However the invention is also applicable to other types of absorbent articles, such as adult incontinent briefs, children training pants and the like.

The portions of the article can be described using the following terms. If the article is spread out flat on a table with the body-touching portion facing up, then the visible surface is referred to as the "top of the article". The surface touching the table is referred to as the "bottom of the article". The near-rectangular portion in the middle of the article is referred to as the "crotch section". The outstretched portion is referred to as the "rear of the article", and more particularly the "bottom-rear" portion of the article covers the buttocks of the wearer. The portion of the article at the other end of the "crotch section" is referred to as the "front portion" of the article. The "bottom-front" portion forms the facing portion of the article.

The present invention improves upon the articles of the prior art by introducing a drawstring-like elastomeric member that covers the whole back as well as the side of the wearer. The instant configuration provides a better fit and grip to the article. The materials that may be used for individual components may be chosen from a wide variety of suitable materials known in this field.

As a general rule, the elastomeric material used in the present invention is stretchable in at least one direction. Preferably, the elastomeric material is stretchable in two directions. When the elastomeric material is stretchable in a single direction, the stretch direction of the elastomeric material will be oriented so as to provide elastomeric forces which tend to pull the front and rear portions of the article towards one another such that the article is maintained about the waist of a wearer. In general, this type of elastomeric material can have a low elasticity such that it generally cannot be enlongated to over 350% before breaking. This elastomeric material can comprise materials such as a stretch-bonded-laminate (SBL) material, a neck-bonded-laminate (NBL) material, an elastomeric film, an elastomeric foam material, spandex, woven elastomeric straps or belts, or the like. For example, suitable meltblown elastomeric fibrous webs are described in U.S. Pat. No. 4,663,220 issued May 5, 1987, to T. Wisneski et al., the disclosure of which is hereby incorporated by reference in its entirety.

As used herein, reference to two materials or elements being "joined" or "attached" refers to a process wherein the two materials or elements are directly joined to one another, or a process wherein the materials are indirectly joined to one another such as where both are joined to an intermediate element. Similarly, methods of joining two materials or elements include forming the elements or materials integrally, or attaching the elements together such as through the use of adhesives, sonic or thermal bonding, sewing, and the like. We shall now explain the invention with reference to the accompanying figures. Although reference herein is made to baby diapers, it will be appreciated that the invention is also applicable to all such products that have a waist region, such as training pants, adult incontinent articles and the like. While the instant invention is described by reference to diapers that have an hourglass-shaped configuration, the invention is also applicable to other kinds of configurations wherein a diaper fit is attained by changing the configuration at the waist, for example, pant-type diapers and the like.

FIG. 1 illustrates an hourglass-shaped absorbent article 10 of this invention. The main body of the article has a front portion 30, a rear portion 40, a crotch portion 20 connecting the front 30 and rear 40 portions, and a rear waist edge 78. The crotch portion 20 is substantially rectangular in shape, and the front 30 and rear 40 portions are adjacent to the shorter edges of the crotch portion 20. It may be noted that the front 30, rear 40, and crotch 20 portions are used herein as merely indicative of various sections of the article. These portions are generally present as one single piece although they have different layers or sheets, and various portions of the article may have one or more layers.

The main body of the article can also have a top sheet 55, a back sheet 60, and an absorbent core 50 disposed therebetween. The top sheet 55, i.e., the layer on the top portion of the article, is a liquid permeable body liner. This is the portion of the article that touches the body of the wearer and it is therefore generally made of a soft material. The bottom sheet 60, i.e., the layer that forms the visible surface of the article, can be a liquid impervious sheet or a pervious hydrophobic sheet, provided that an impervious sheet is also used beneath the absorbent core 50. Interposed between these layers is an absorbent core 50 that has the functionality to absorb the body fluids. The rear portion 40 spans outwards forming ears 80 at the respective left and right edges of the absorbent article. Fasteners 90 are intended to engage coupling members 75 on the left and right edges of the front portion 30 of the article or across the entire front portion 30.

When a diaper is fastened to the body of a wearer, the diaper is fastened in such a manner that the crotch region 20 of the diaper covers the crotch portion of the wearer. As mentioned earlier, the surface of the diaper that touches the body of the wearer is the liquid pervious top sheet 55. The front portion 30 is pulled over to the front portion of the body of the diaper such that it covers the area of the stomach below the navel. The rear portion 40 covers the bottom of the wearer. The ears 80 are pulled over from behind such that they cover the side portion of the body using fasteners 90 that are fixed to coupling members 75 on the front portion 30 of the diaper. Consequently, the left and right ears 80, the waist edge of the rear portion 78, and the front portion 75, form a waist circle for the wearer. Additionally, the edges of the crotch portion 20 together with the ears 80 form the leg openings for the wearer. The article is further provided with elastic members 67, 70, and 85 so as to have a better fit. The tightening of the article around the waist is assisted by this elastomeric material and the ears 80 together with the fasteners 90 and 75. The fastening can be done at an appropriate place so as to form the exact waist size of the wearer. Furthermore, the article is also provided with elastic members 65 at the sides so as to prevent leakage from the sides. Leakage is prevented by the presence of members 67 and 70 at the top and bottom of the rear 40 and front 30 portions, respectively.

The center 101 of an elastomeric member 100 is attached to the article near the longitudinal axis 102 of the article. This elastomeric member 100 spans outwards so as to form ear-like projections A1 and B1 at either edges of the absorbent article. Regions A1 and B1 denote the left and right elastomeric ear-like projections of the article, and regions A2 and B2 are the portions of the elastomeric member 100 that cover the rear portion 40 of the article. Such a configuration makes the elastomeric member independently stretchable from the rear portion of the article (except for the attachment portion), and hence offers a much better fit to the article around the waist. The attachment as mentioned herein may be done by a variety of suitable means such as by using adhesives, heat fusion, stitching, etc.

In the prior art disposable articles, stretching is primarily achieved through the ear portion 80, which puts a strain on the side portion of the body of the wearer. However, in the instant invention, the stress force as a result of stretching the elastomeric member 100 is distributed from the longitudinal axis 102 to the outer edges of the article (see arrows), minimizing the stress and pull on the body of the wearer. The reduction in this force makes the article less irritable to the skin, thereby increasing its capacity for prolonged wear.

Since the length of stretching required from the elastomeric member 100 is now distributed over a greater length i.e., (A1+A2+B1+B2)>(A1+B1), the elastomeric member 100 used may be less extensive and consequently, less costly, thereby reducing the overall cost of the article.

Figure 2:
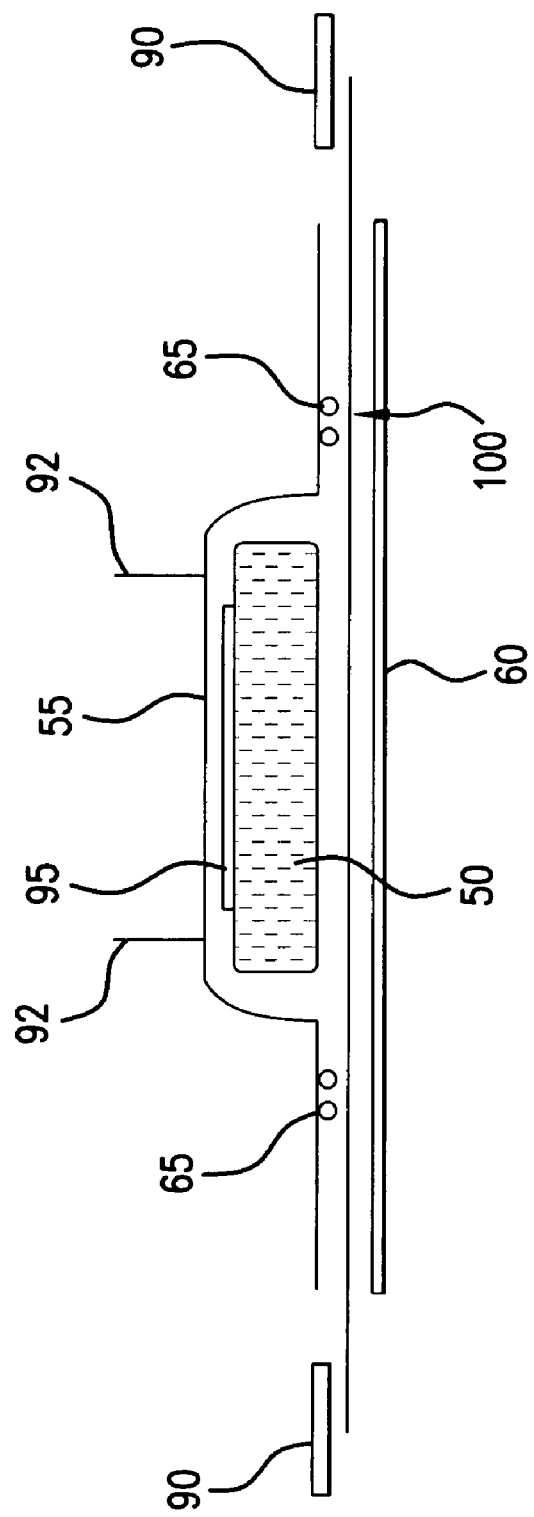
FIG. 2 is the longitudinal cross section of the absorbent article of the embodiment of FIG. 1.

FIG. 2 shows the cross section of the article shown in FIG. 1. The bottom most layer is the liquid impermeable outer sheet 60 having outstretched ears 80 (not shown) with fasteners 90 attached to regions A1 and B1 of the elastomeric member 100, respectively. This outer sheet 60 may be made from materials that are impermeable to liquids so that the liquid (body fluid) retained in the absorbent core 50 does not escape through it. It may be manufactured from various kinds of polymers that are thin as well as comfortable to fold and feel. Furthermore, the outer sheet 60 may be patterned or printed so as to increase the visual appeal of the article. The fasteners 90 may be mechanical fasteners or tapes, etc. Mechanical fasteners include fasteners such as loops, hooks, buttons, snaps, latches, etc. The fastener 90 is used in coupling with its mating member 75 attached to the front of the article. For example, the fastener 90 could have the hook and the mating member 75 could have the loop in a typical hook and loop assembly.

The top layer in FIG. 2 is the liquid permeable body sheet 55. The body side liner is made from a material that is not only porous for the body fluids ("insult") to pass through, but is also soft to the skin. It may be made from any kind of woven or non-woven material, or a combination of these materials. The absorbent core 50 is attached between the outer sheet 60 and the top sheet 55. These two layers are predominantly in the crotch portion 20 of the article. The core has a top that is the absorbent surface 95. This surface has fast absorption properties that quickly absorbs any discharged body fluid, which is then gradually absorbed by the absorbent core 50. The absorbent core 50 retains the fluid until the article is disposed of. The absorbent core 50 is made from various kinds of natural or synthetic hydrophilic materials having particle shapes and sizes so as to offer maximum absorption area and liquid retention duration. The absorbent core 50 may be interposed with high absorbent materials such as silica gel, etc., so as to increase the liquid retention capacity. The top surface of the core 95 may have an absorbent surface made from a material that absorbs the liquid much faster than the core 50, and transfers it to the core 50 over a period of time.

The side portion of the article has elastic members 65 and leg cuffs 92 that result in a better fit of the diaper around the legs as well as preventing any leakage from the sides. The elastic members 65 are formed by thin strands of elastic that collectively form the side portions of the article. The leg elastics 65 may be straight, curved or gathered as desired so as to provide better covering to the under leg and thigh portion of the wearer.

The elastomeric member 100 is interposed between the non-permeable back sheet 60 and the liquid permeable top sheet 55. The length of the elastomeric member 100 can extend beyond the length of the rear portion 40 of the article so as to form ear-like projections A1 and B1.

Figure 3:
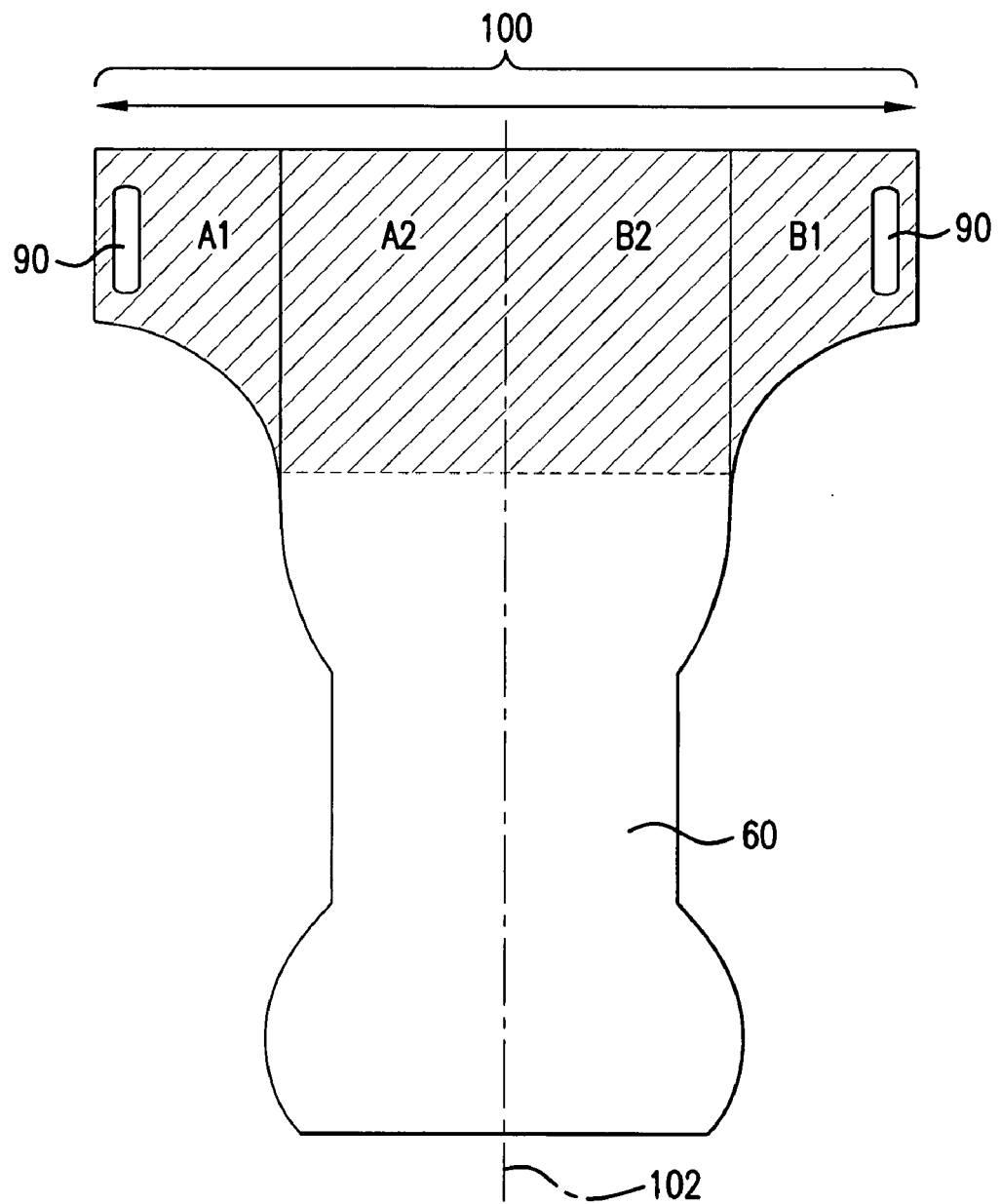
FIG. 3 is the rear view of the embodiment of the absorbent article illustrated in FIG. 1.

FIG. 3 shows the back view of a first embodiment of the article wherein the outer sheet 60 completely covers (but is not attached to) the elastomeric member 100. In such a configuration, the appearance of the article is not affected. Furthermore, in FIGS. 3, 5, 6 and 7, the elastomeric member 100 is one single piece attached only at its center to near the longitudinal axis 102 of the article. From near the axis, it projects to either side of the article and forms ear-like projections A1 and B1 at the right and left edges of the article, respectively.

Figure 4:
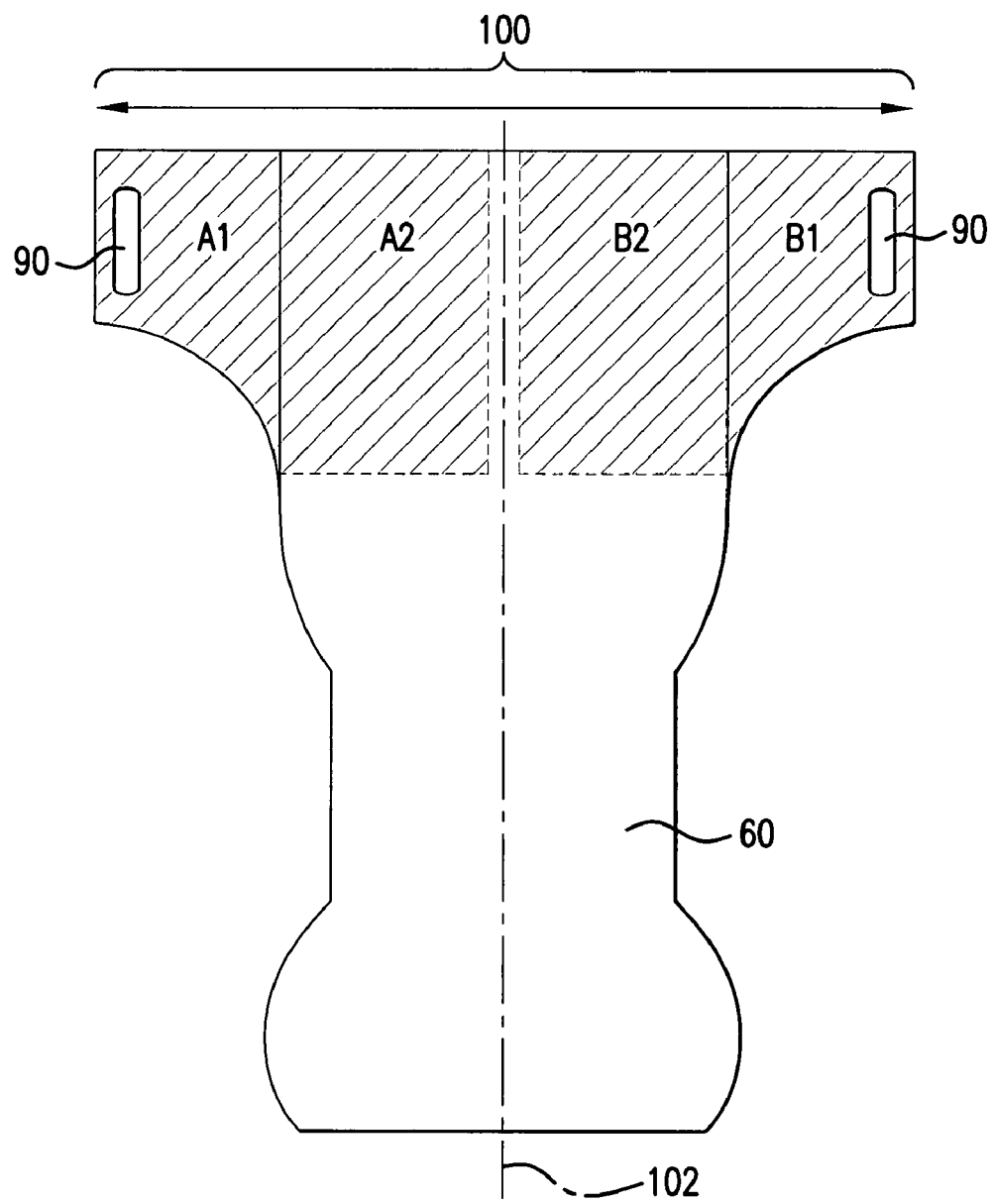
FIG. 4 is the rear view of another embodiment of the invention.

FIG. 4 shows the configuration of the article of the second embodiment of the invention. In this embodiment the elastomeric member 100 is a two-piece article, one piece A1+A2 of which is attached to the right side of the longitudinal axis 102 of the article at one end, and spans outwardly to the right side of the article forming a right ear-like projection A1. The other side B1+B2 is attached to the left side of the longitudinal axis at one end and forms the left ear-like projection B1 of the article. In the aforementioned embodiments, the elastomeric member 100 is cut in the shape of the rear portion of the article, i.e., in the shape of outstretched ears 80 reaching from the crotch portion of the diaper. Furthermore, the elastomeric member 100 is sandwiched between the outer sheet 60 and the body liner 55.

Figure 5:
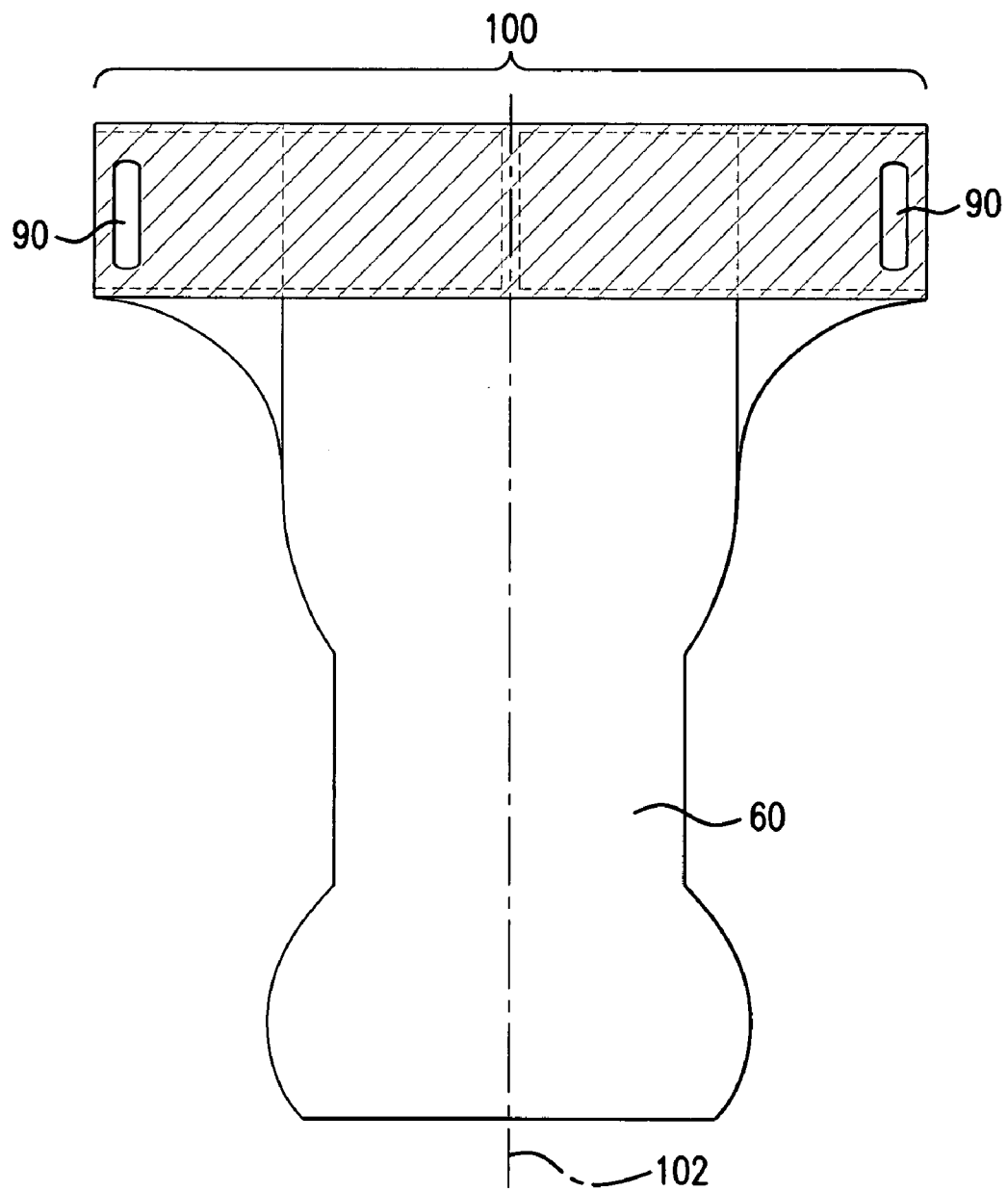
FIG. 5 is the rear view of a further embodiment of the invention.

FIG. 5 shows another embodiment of the article in which a belt-like elastomeric member 100 is attached as the outermost layer extending over the outer sheet 60 of the article. As seen in the figure, the rear of the article is shaped like ears, and the belt-like elastomeric member 100 covers (but is not attached to) the length of these ears 80, thereby ensuring that any stretching applied on this member would stretch the belt-like elastomeric member 100 independently from these ears 80. The same belt-like configuration may also be sandwiched between the outer sheet 60 and body liner 55. Since the material used in the belt-like configuration is less than in a conventional design, further savings in costs are achieved.

Figure 6:
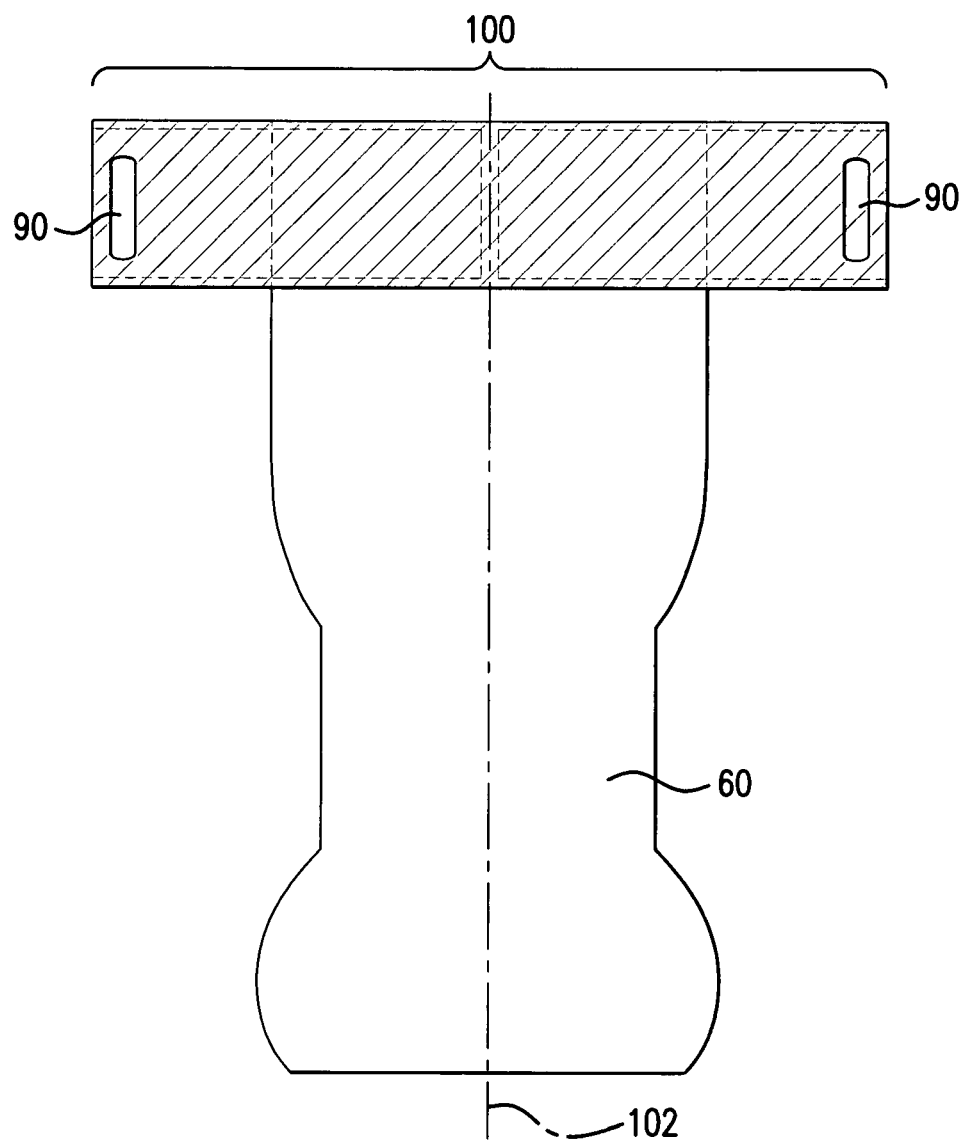
FIG. 6 is the rear view of a still further embodiment of the invention.

FIG. 6 shows yet another embodiment of the invention in which the rear portion 40 of the article has an attractive shape, and just covers the rear part of the body not the side. In contrast to FIG. 1, here the rear portion 40 of the article does not have ears 80 and the fastener 90 is attached to the elastomeric member 100. The elastomeric member 100 is shaped like a belt and spans to either side of the article. The elastomeric member 100 just covers the waist region of the side of the body and fastens to the front portion 30 of the article.

Figure 7:
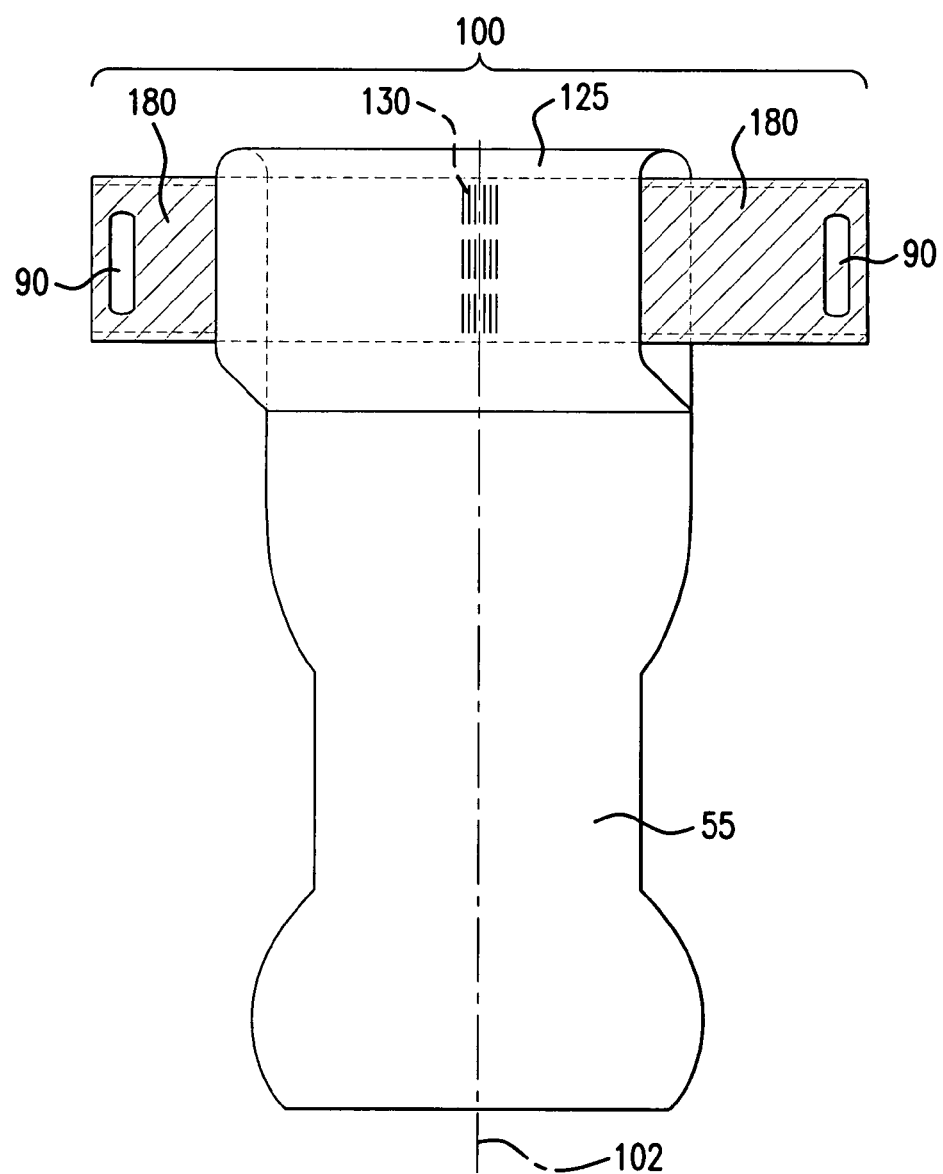
FIG. 7 is a top view of another embodiment of an absorbent article.

FIG. 7 shows yet another embodiment of the absorbent article in which the elastomeric member 100 has a central portion 130 and a pair of opposite free ends each defining ear-like projections 180. The central portion 130 is disposed in a sleeve-like member 125 with each ear-like projection 180 extending out from opposite sides of the sleeve-like member 125. The sleeve-like member 125 can extend adjacent the waist edge of the front portion (not shown) or the waist edge of the rear portion 78. The central portion 130 can be attached by adhesives, heat fusion, stitching or the like to near the longitudinal axis 102 of the sleeve-like member 125 or adjacent the waist edge of the rear portion 78. The ear-like projections 180 can extend beyond the edges of the front 30 or rear 40 portions. A fastener 90 can be attached to each ear-like projection 180. The ear-like projections 180 can be attachable to each other and/or the main body to form the desired waist size of a wearer of the absorbent article. The elastomeric member 100 can be independently stretchable of the main body and the sleeve-like member 125.

The sleeve-like member 125 can be formed from or attached to the back sheet 60, the top sheet 55, or an outer surface of the back sheet 60. The sleeve-like member 125 can be formed by folding a waist edge of these sheets towards the crotch portion. The sleeve-like member 125 can be disposed intermediate the top sheet 55 and back sheet 60. In another embodiment, the main body can have at least one additional layer, and the sleeve-like member can be formed from or attached to this additional layer. The sleeve-like member 125 can be formed by folding the waist edge of this additional layer towards the crotch portion. The embodiment depicted in FIG. 7 can generally work in a similar manner as described previously in connection with embodiment 10 depicted in FIG. 1.

In an alternative embodiment, the elastomeric member can have a pair of elastomeric members each having one end retained within the sleeve-like member and an opposite free end defining a pair of ear-like projections, one ear-like projection extending from opposite ends of the sleeve-like member. In another embodiment, the article can have a pant-like structure in which the front and rear portions are permanently connected to each other along transversely opposite lateral edges so as to define a waist-opening and a pair of leg-openings.

As can be seen from the above-illustrated embodiments, the article of this invention can include many different configurations. The aforementioned embodiments are merely illustrative and are not intended to limit the scope of the invention in any way. Various alternatives of the invention may exist, and the invention seeks to cover all such equivalents, including equivalents embodying the use of various materials. As may be apparent to those skilled in the art, various embodiments of the invention can be conceived and applied to various forms of absorbent articles without departing from the spirit, crux and focus of the invention. Accordingly, the scope of the invention is not bound by the appended claims, but includes all permissible equivalents therefore.

What is claimed is:

1. A disposable absorbent article comprising:
   a main body having a front portion, a rear portion and a crotch portion intermediate said front and rear portions, said front and rear portions each having a waist edge and lateral side edges;
   a sleeve-like member extending adjacent said waist edge of at least one of said front and rear portions and substantially through said at least one of said front and rear portions; and
   an elastomeric member having a central portion and a pair of opposite free ends each defining ear-like projections that are integral with the elastomeric member, said central portion disposed at least partially in said sleeve-like member with said ear-like projections extending out from opposite sides of said sleeve-like member and beyond said lateral side edges of the at least one of said front and rear portions; and
   wherein said ear-like projections are attachable to at least one of each other and said main body to form a desired waist size of a wearer of the absorbent article.

2. The article of claim 1 further comprising said central portion attached to at least one of said sleeve-like member, said front portion, and said rear portion.

3. The article of claim 2 wherein said central portion is attached to at least one of: near a longitudinal axis of said main body; and adjacent said waist edge of said rear portion.

4. The article of claim 3 further comprising: said main body having a top sheet, a back sheet, and an absorbent core disposed at least partially therebetween; and
   wherein said sleeve-like member is formed from or attached to at least one of said back sheet and said top sheet.

5. The article of claim 4 further comprising said sleeve-like member disposed intermediate said top sheet and back sheet.

6. The article of claim 4 further comprising said sleeve-like member formed from or attached to an outer surface of said back sheet.

7. The article of claim 6 wherein said sleeve-like member is formed by folding said waist edge of said back sheet towards said crotch portion.

8. The article of claim 4 wherein said main body further comprises at least one additional layer, and said sleeve-like member is formed from or attached to said at least one additional layer.

9. The article of claim 8 wherein said at least one additional layer has a waist edge, and said sleeve-like member is formed by folding said waist edge of said at least one additional layer towards said crotch portion.

10. The article of claim 1 wherein said elastomeric member is at least partially independently stretchable of said main body and said sleeve-like member.

11. The article of claim 1 wherein said elastomeric member further comprises:
   a pair of elastomeric members;
   each of said pair of elastomeric members having one end retained within said sleeve-like member and an opposite free end extending from said sleeve-like member and defining an ear-like projection;
   said ear-like projection of each of said pair of elastomeric members extending from opposite ends of said sleeve-like member such that said ear-like projections are attachable to at least one of each other and said main body to form the desired waist size of a wearer of the absorbent article.

12. The article of claim 11 further comprising said one end of each of said pair of elastomeric members is attached to at least one of said sleeve-like member and at least one of said front and rear portions.

13. The article of claim 12 wherein said one end of each of said pair of elastomeric members is attached to at least one of: near a longitudinal axis of said main body; and adjacent said waist edge of said rear portion.

14. The article of claim 13 further comprising:
   said main body having a top sheet, a back sheet, and an absorbent core disposed at least partially therebetween; and
   wherein said sleeve-like member is formed from or attached to at least one of said back sheet and said top sheet.

15. The article of claim 14 further comprising said sleeve-like member disposed intermediate said top sheet and back sheet.

16. The article of claim 14 further comprising said sleeve-like member formed from or attached to an outer surface of said back sheet.

17. The article of claim 16 wherein said sleeve-like member is formed by folding said waist edge of said back sheet towards said crotch portion.

18. The article of claim 14 wherein said main body further comprises at least one additional layer, and said sleeve-like member is formed from or attached-to said at least one additional layer.

19. The article of claim 18 wherein said at least one additional layer has a waist edge, and said sleeve-like member is formed by folding said waist edge of said at least one additional layer towards said crotch portion.

20. The article of claim 1 wherein said elastomeric member is attached by at least one of adhesives, heat fusion, and stitching.

21. The article of claim 1 further comprising a fastener attached to each of said ear-like projections.

22. The article of claim 21 wherein said fastener is selected from the group consisting of buttons, adhesive tapes, hooks and loops, snaps and latches, and combinations thereof.

23. The article of claim 1 wherein said article is a diaper.

24. The article of claim 1 wherein said article has a pant-like structure, and wherein said front and rear portions are permanently connected to each other along transversely opposite lateral edges thereof so as to define a waist-opening and a pair of leg-openings.

25. The article of claim 1 wherein said elastomeric material has low elasticity such that said elastomeric material generally cannot be enlongated to over 350% before breaking.

26. The article of claim 25 wherein said elastomeric material is selected from the group consisting of stretch-bonded laminate material, neck-bonded-laminate material, elastomeric strands, elastomeric films, elastomeric foam material, spandex, woven elastomeric straps or belts, and combinations thereof.

* * * * *